United States Patent
Kim et al.

(10) Patent No.: US 12,121,398 B2
(45) Date of Patent: Oct. 22, 2024

(54) IMAGING AND THERAPY INTEGRATED TRANSDUCER AND ULTRASOUND SYSTEM COMPRISING SAME

(71) Applicant: POSTECH RESEARCH AND BUSINESS DEVELOPMENT FOUNDATION, Pohang-si (KR)

(72) Inventors: Hyung Ham Kim, Pohang-si (KR); Hae Gyun Lim, Pohang-si (KR); Hyun Hee Kim, Pohang-si (KR)

(73) Assignee: POSTECH RESEARCH AND BUSINESS DEVELOPMENT FOUNDATION, Pohang-si (KR)

( * ) Notice: Subject to any disclaimer, the term of this patent is extended or adjusted under 35 U.S.C. 154(b) by 0 days.

(21) Appl. No.: 17/768,531

(22) PCT Filed: Jul. 27, 2020

(86) PCT No.: PCT/KR2020/009833
§ 371 (c)(1),
(2) Date: Apr. 13, 2022

(87) PCT Pub. No.: WO2021/075676
PCT Pub. Date: Apr. 22, 2021

(65) Prior Publication Data
US 2024/0108310 A1 Apr. 4, 2024

(30) Foreign Application Priority Data
Oct. 14, 2019 (KR) .................. 10-2019-0127026

(51) Int. Cl.
*A61B 8/00* (2006.01)
*A61N 7/00* (2006.01)
*A61N 7/02* (2006.01)

(52) U.S. Cl.
CPC .......... *A61B 8/4494* (2013.01); *A61B 8/4461* (2013.01); *A61B 8/54* (2013.01);
(Continued)

(58) Field of Classification Search
CPC ....... A61B 8/4494; A61B 8/4488; A61B 8/54; A61N 7/00; A61N 7/02; A61N 2007/0082
See application file for complete search history.

(56) References Cited

U.S. PATENT DOCUMENTS

| | | | | |
|---|---|---|---|---|
| 5,720,287 | A | * | 2/1998 | Chapelon ............ A61N 7/022 600/459 |
| 2011/0181149 | A1 | * | 7/2011 | Shikata ............ G10K 11/004 310/327 |
| 2014/0180103 | A1 | * | 6/2014 | Sinelnikov ............ A61B 8/485 310/317 |

FOREIGN PATENT DOCUMENTS

| | | |
|---|---|---|
| JP | 19970503926 | 4/1997 |
| JP | 2004534624 | 11/2004 |

(Continued)

*Primary Examiner* — Chao Sheng
(74) *Attorney, Agent, or Firm* — LEX IP MEISTER, PLLC

(57) ABSTRACT

An ultrasound system according to an embodiment of the present invention includes an imaging and therapy integrated transducer including a therapy transducer and an imaging transducer, a linear motor module configured to linearly move the imaging and therapy integrated transducer along a therapy target region, and a rotation motor module configured to rotate the imaging and therapy integrated transducer to switch the imaging transducer and the therapy transducer, wherein the therapy transducer and the imaging transducer are arranged to be switchable to each other by rotation in a housing.

7 Claims, 3 Drawing Sheets

(52) U.S. Cl.
CPC ................ *A61N 7/00* (2013.01); *A61N 7/02* (2013.01); *A61N 2007/0082* (2013.01)

(56) References Cited

FOREIGN PATENT DOCUMENTS

| | | |
|---|---|---|
| JP | 2006061448 | 3/2006 |
| KR | 20110079096 | 7/2011 |
| KR | 20130133121 | 12/2013 |

\* cited by examiner

100

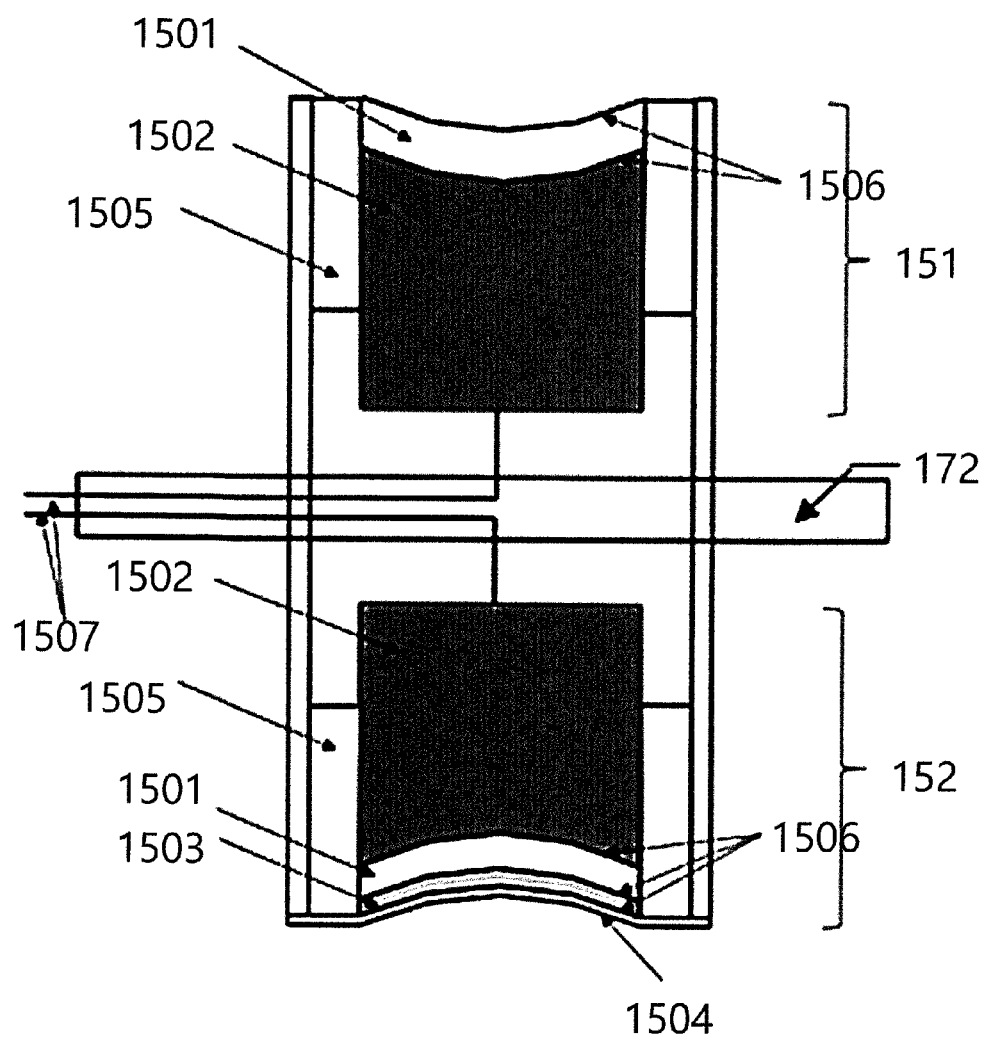

IMAGING AND THERAPY INTEGRATED TRANSDUCER AND ULTRASOUND SYSTEM COMPRISING SAME

TECHNICAL FIELD

The present invention relates to an imaging and therapy integrated transducer and an ultrasound system including the imaging and therapy integrated transducer.

BACKGROUND ART

A sound wave with a frequency of 20 kHz or higher, which is a frequency band higher than a human audio frequency range, is called an ultrasound wave, and an image generated by interpreting a received signal generated through diffusion, reflection, absorption, and scattering of sound waves at various interfaces such as internal organs, bones, muscle tissue, and blood by using the ultrasound wave is called an ultrasonic image.

Most of the current ultrasound imaging devices that are common at home and abroad use ultrasound waves of a low-frequency bandwidth (2 to 10 MHz). Low-frequency ultrasound imaging devices provide a relatively low resolution, and thus, the devices may not accurately diagnose microorganisms such as small-sized organs and tumors. In contrast to this, high-frequency (10 MHz or higher) ultrasound imaging devices provide a high resolution, and thus, the devices may image tissues that are difficult to diagnose with low-frequency ultrasound images, such as laparoscopy, endoscopy, ophthalmology, dermatology, and intravascular imaging, with a high resolution. However, a high level of precision is required in a manufacturing process of a transducer which is a key element of high-frequency ultrasound imaging, and thus, only a small number of manufacturing companies in the world possess the relevant technology and release products.

In addition, today, studies are being actively attempted to treat diseases in a non-invasive method outside the body by using ultrasound aside from the field of diagnosing diseases. A typical therapy method using ultrasound includes a method of increasing a temperature of body tissue by using high-intensity focused ultrasound (HIFU) to induce necrosis of cells or to remove tissues by exposing the tissues to high temperature in a short time. A temperature of an organ may be increased by using HIFU within a few seconds, and a part of the tissue may be necrotic through exposure to a temperature of 55 degrees or more for about 1 second. Such ultrasound therapy has advantages in which a procedure may be performed while a patient is awake, surrounding tissues are not affected, a patient has less pain, and other substances are not required to be injected into the body. In addition, various organs such as tumors, liver, kidneys, bones, and rectum may be accessed. Various therapies are also being attempted, and in addition to a method of directly increasing the tissue temperature, it also induces cellular changes according to changes in the living environment by increasing a temperature of a region near the tissue.

A non-invasive surgical system using laser, radiation, and so on in addition to the ultrasound, and a minimally invasive surgical method using laparoscopy and endoscopy are more commonly used than the known incisional surgery methods. However, such a non-invasive or minimally invasive method has a disadvantage in that it is not possible to check a state change in the field before and after surgery.

An ultrasound therapy device and an ultrasound imaging device may be used together to check a state change before and after surgery, but in this case, it is necessary to separately provide an ultrasound transducer for therapy and an ultrasound transducer for imaging, and furthermore, there is a limitation in that it is difficult to accurately acquire an image of a therapy region.

DISCLOSURE

Technical Problem

Therefore, the technical field requires a method of performing ultrasound therapy and ultrasound image acquisition by using a single device and to quickly and accurately acquire images of a therapy region before and after ultrasound therapy.

Technical Solution

In order to solve the above problems, an embodiment of the present invention provides an ultrasound system.

The ultrasound system includes an imaging and therapy integrated transducer including a therapy transducer and an imaging transducer, a linear motor module configured to linearly move the imaging and therapy integrated transducer along a therapy target region, and a rotation motor module configured to rotate the imaging and therapy integrated transducer to switch the imaging transducer and the therapy transducer, wherein the therapy transducer and the imaging transducer are arranged to be switchable to each other by rotation in a housing.

In addition, means for solving the above problems do not enumerate all the features of the present invention. Various features of the present invention and advantages and effects thereof may be understood in more detail with reference to the following specific embodiments.

Advantageous Effects

According to an embodiment of the present invention, it is possible to perform ultrasound therapy and ultrasound image acquisition by using a single device and to quickly and accurately acquire images of a therapy region before and after ultrasound therapy at a treated location without moving a transducer after ultrasound therapy.

In other words, when a center shaft rotates 180 degrees, a focal point located on the same axis, that is, a therapy region may be diagnosed more accurately and precisely by miniaturizing individual devices with similar focal depths and further improved resolution, and the most appropriate diagnosis and therapy are possible by arranging the devices in a switchable form.

Through this, changes in lesions and therapy effects may be determined by high-resolution images immediately before and after each step among various steps of therapy, and thus, it is possible to immediately determine whether therapy is appropriate and determine whether additional therapy is required and the intensity of therapy should be adjusted.

DESCRIPTION OF THE DRAWINGS

FIG. 3 is a diagram illustrating a structure of the imaging and therapy integrated transducer according to the embodiment of the present invention.

MODE FOR INVENTION

Figure 1:
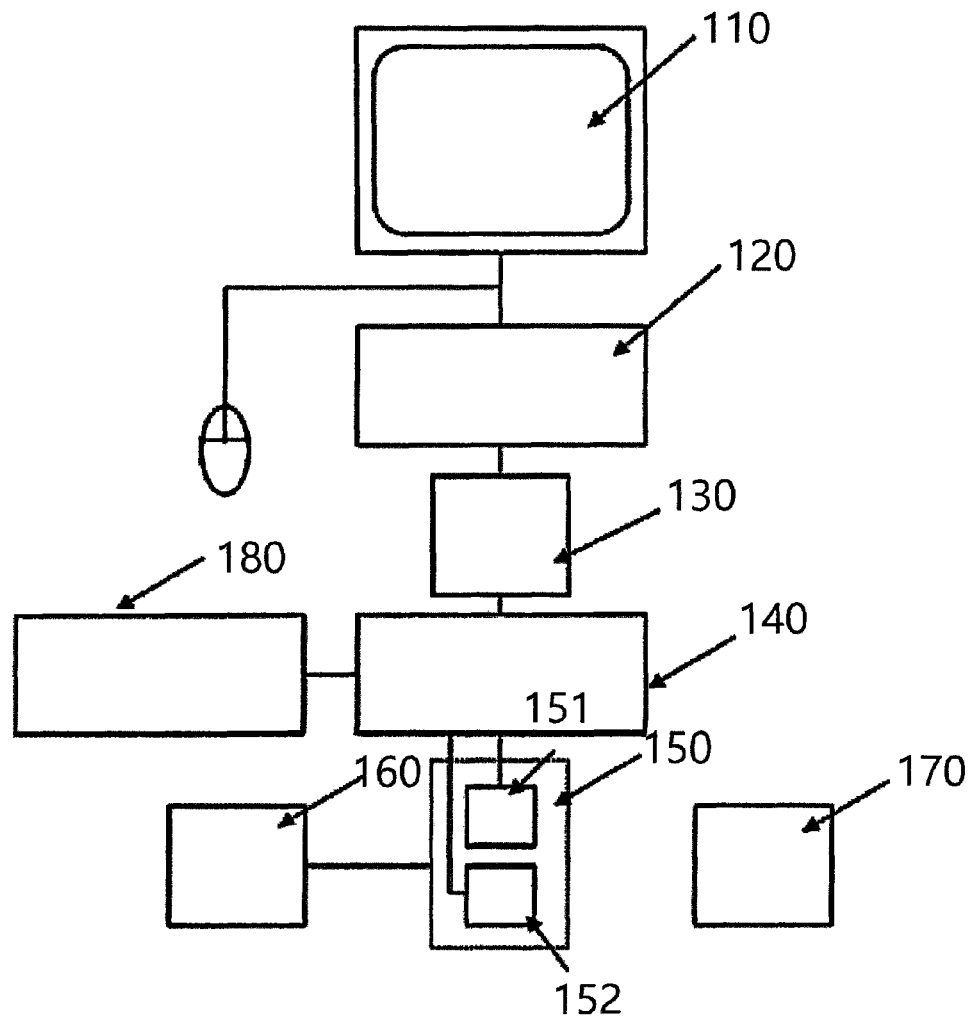
FIG. 1 is a diagram illustrating an ultrasound system according to an embodiment of the present invention.

Hereinafter, preferred embodiments will be described in detail with reference to the accompanying drawings such that those skilled in the art may easily implement the present invention. However, in describing the preferred embodiment of the present invention in detail, when it is determined that detailed descriptions of a related known function or configuration may unnecessarily obscure the idea of the present invention, the detailed descriptions thereof are omitted. In addition, the same reference numerals are used throughout the drawings for components that perform similar functions and operations.

In addition, throughout the specification, when it is described that a region is "connected" to another region, this includes not only a case of being "directly connected" to another region but also a case of being "indirectly connected" thereto with another component therebetween. In addition, "including" a certain component means that other components may be further included, rather than excluding other components, unless otherwise stated.

According to an embodiment of the present invention, an imaging ultrasound transducer and a therapy ultrasound transducer have to be manufactured to implement an integrated transducer that may perform imaging diagnosis and therapy.

An ultrasound transducer for therapy requires a high-intensity ultrasound beam to increase a tissue temperature in a short time to acquire a thermotherapy effect, and an ultrasound transducer for imaging requires a frequency of 10 MHz or higher in order to image changes in tissue due to focused heat therapy with a high resolution.

In addition, a switchable housing is required to integrate the therapy ultrasound transducer and the imaging ultrasound transducer into one device.

Hereinafter, an imaging and therapy integrated transducer and an ultrasound system including the imaging and therapy integrated transducer according to an embodiment of the present invention will be described in detail with reference to FIGS. 1 to 3.

FIG. 1 is a diagram illustrating an ultrasound system according to an embodiment of the present invention.

Referring to FIG. 1, an ultrasound system 100 according to an embodiment of the present invention includes a display module 110, an image module 120, a data collection module 130, a signal amplifier 140, an imaging and therapy integrated transducer 150, a linear motor module 160, a rotation motor module 170, and a signal generator 180.

The display module 110 displays an ultrasound diagnosis image captured by the ultrasound system 100.

According to an example, the display module 110 may display a high-resolution ultrasound diagnostic image captured by the image module 120 to enable a therapy region to be diagnosed.

The image module 120 generates a high-resolution image of data collected by the data collection module 130.

The data collection module 130 collects data for image diagnosis by ultrasound generated by the imaging and therapy integrated transducer 150.

The signal amplifier 140 amplifies a signal generated by the signal generator 180 or so on.

The imaging and therapy integrated transducer 150 transduces electrical energy into sound wave energy and includes a therapy transducer 151 and an imaging transducer 152 to enable both therapy and imaging diagnosis.

Here, the therapy transducer 151 and the imaging transducer 152 have a similar focal depth (that is, have the same focal depth or have a difference within a preset range) and may be arranged to be switchable to each other by rotation in a housing.

In addition, the imaging transducer 152 may have a frequency of 10 MHz or higher to acquire a high-resolution image.

A detailed structure of the imaging and therapy integrated transducer 150 and a driving method thereof will be described in detail below with reference to FIGS. 2 and 3.

The linear motor module 160 linearly moves the imaging and therapy integrated transducer 150 and may be implemented as, for example, a stepping motor or so on to linearly move the imaging and therapy integrated transducer 150 along a therapy region.

The rotation motor module 170 may rotate the imaging and therapy integrated transducer 150 to switch the imaging transducer 152 and the therapy transducer 151, and for example, the rotation motor module 170 may rotate the imaging and therapy integrated transducer 150 by 180 degrees to enable one of the imaging transducer 152 and the therapy transducer 151 to face a therapy target region of a human body.

The signal generator 180 generates a signal for driving the imaging and therapy integrated transducer 150.

The components included in the ultrasound system 100 illustrated in FIG. 1, except for the imaging and therapy integrated transducer 150, the linear motor module 160, and the rotation motor module 170, may be implemented by technology known to those skilled in the art, and thus, detailed descriptions thereof are omitted.

Figure 2:
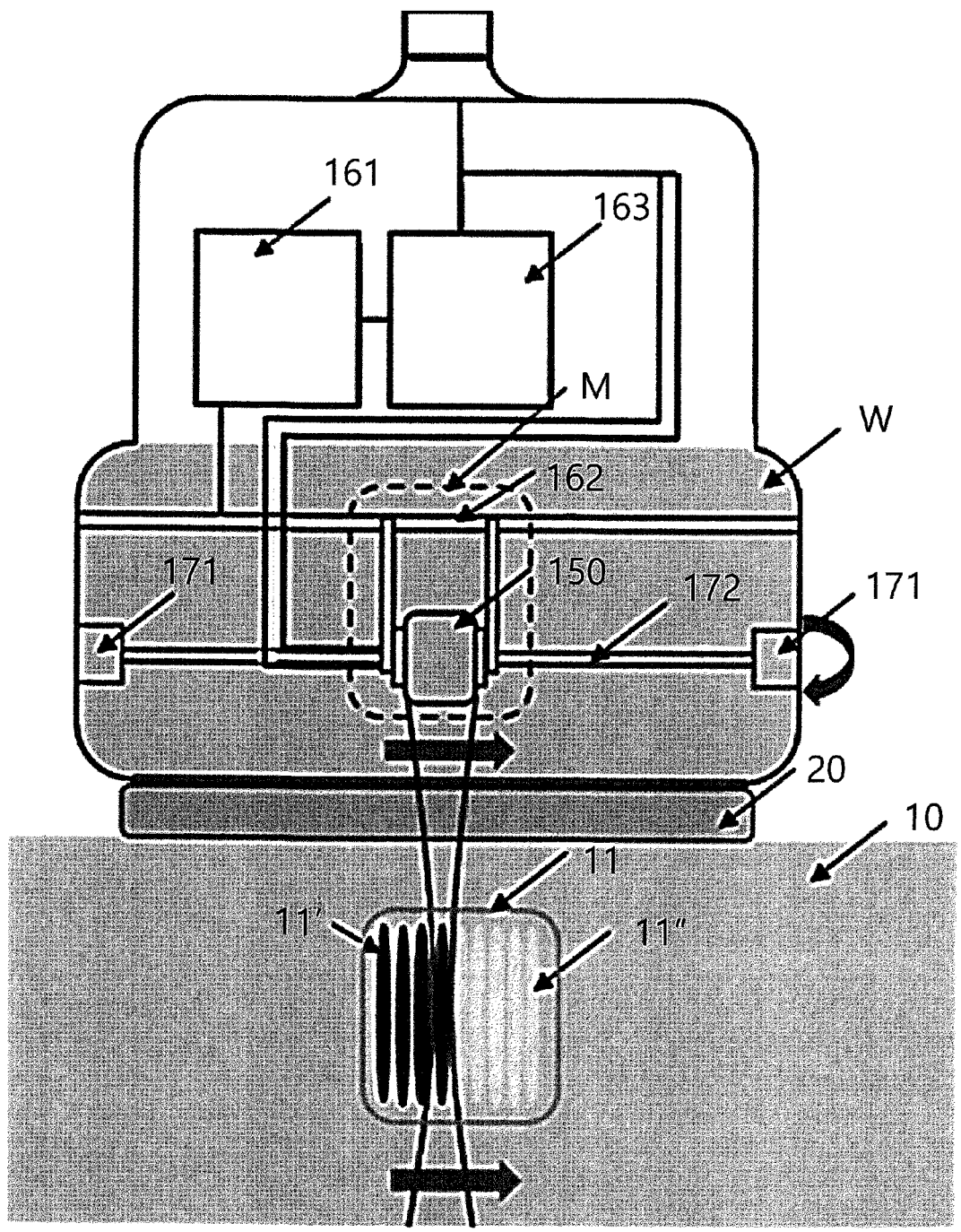
FIG. 2 is a diagram illustrating a linear scan drive of an imaging and therapy integrated transducer of an ultrasound system according to an embodiment of the present invention.

FIG. 2 is a diagram illustrating a linear scan drive of an imaging and therapy integrated transducer of an ultrasound system according to an embodiment of the present invention.

Referring to FIG. 2, a movement unit M including the imaging and therapy integrated transducer 150 moved by using a linear motor shaft 162 and a rotary motor shaft 172 as axes.

First, the imaging and therapy integrated transducer 150 controls an imaging transducer included therein to face a human body 10 in order to perform pre-therapy diagnosis. Distilled water W is filled in the housing, and ultrasound gel 20 is applied to a space between the housing and the human body 10. The movement unit M images a therapy target region 11 of the human body 10 while linearly moving along an axis by a linear motor 161.

After that, when the movement unit M reaches a rotation motor 171 located at one end of the rotary motor shaft 172, the imaging and therapy integrated transducer 150 rotates 180 degrees by the rotation motor 171 such that a therapy transducer included in the imaging and therapy integrated transducer 150 faces the therapy target region 11.

After that, the movement unit M makes therapy of the therapy target region 11 while moving to an opposite side by using the linear motor shaft 162 and the rotary motor shaft 172 as axes in the same manner as before. Here, 11' denotes a region for which therapy is made, and 11" denotes a region for which therapy is going to be made.

After that, when the movement unit M reaches the rotation motor 171 located at the other end of the rotary motor shaft 172, the imaging and therapy integrated transducer 150 rotates 180 degrees again by the rotation motor 171 such that an imaging transducer included in the imaging and therapy integrated transducer 150 faces the therapy target region 11.

After that, the movement unit M images the therapy target region 11 while linearly moving along the axis by the linear motor 161 to acquire an image of the region for which therapy is made.

The linear motor 161 and the rotation motor 171 may be controlled by a motor control unit 163 so as to be driven as described above.

As described above, a therapy effect may be immediately checked by simply acquiring images of the therapy region before and after ultrasound therapy.

FIG. 3 is a diagram illustrating a structure of an imaging and therapy integrated transducer according to an embodiment of the present invention.

Referring to FIG. 3, the imaging and therapy integrated transducer 150 according to an embodiment of the present invention includes the therapy transducer 151 and the imaging transducer 152 arranged in a straight line to face each other in an opposite direction based on the rotary motor shaft 172. Accordingly, the therapy transducer 151 and the imaging transducer 152 may be switched to each other while rotating around the rotary motor shaft 172 by 180 degrees.

The therapy transducer 151 and the imaging transducer 152 may be manufactured by lapping front and rear surfaces of piezoelectric elements 1501 with a thickness preset by a frequency and by performing casting and stacking on the front and rear surfaces of the piezoelectric elements 1501.

First, the therapy transducer 151 has a form in which a conductive material 1506, the piezoelectric element 1501, a conductive material 1506, and a rear surface layer 1502 are sequentially stacked, and both sides of the stacked elements may be protected by an epoxy resin 1505. In addition, a wire 1507 for transferring a signal may be connected to the rear surface layer 1502.

In addition, the imaging transducer 152 has a form in which a second matching layer 1504, a conductive material 1506, a first matching layer 1503, a conductive material 1506, the piezoelectric element 1501, a conductive material 1506, and a rear surface layer 1502 are sequentially stacked, and both sides of the stacked elements may be protected by an epoxy resin 1505. In addition, a wire 1507 for transferring a signal may be connected to the rear surface layer 1502.

Here, thicknesses of the second matching layer 1504 and the first matching layer 1503 may be optimized near a thickness of a quarter of a wavelength of a center frequency of an ultrasonic wave to be used to match acoustic impedance. In addition, any material with a lower acoustic impedance than acoustic impedance of the piezoelectric element 1501 may be processed and used without limitation as materials of the second matching layer 1504 and the first matching layer 1503.

In addition, the piezoelectric element 1501 may be optimized near a thickness of half the wavelength of the center frequency of the ultrasonic wave to be used. In addition, a piezoelectric crystal element is mainly used as the piezoelectric element 1501, and the piezoelectric crystal element includes, for example, a monocrystalline structure such as lithium niobate ($LiNbO_3$), a polycrystalline structure such as lead zirconate titanate (PZT), a thin film such as zinc oxide (ZnO), a polymer structure such as polyvinylidene fluoride (PVDF), and a composite structure. In addition, a piezoelectric composite in which a material such as epoxy is mixed with a piezoelectric crystal element may also be used as the piezoelectric element 1501.

When an electrical signal is applied to the conductive material 1506, ultrasonic waves are generated, and the first matching layer 1503 and the second matching layer 1504 included in the imaging transducer 152 reduce loss of ultrasonic waves caused by a difference in acoustic impedance. In addition, the rear surface layer 1502 absorbs ultrasonic waves.

In addition, the therapy transducer 151 and the imaging transducer 152 may share the same rear surface layer 1502 with each other.

FIG. 3 illustrates a case in which both a therapy transducer and an imaging transducer included in an imaging and therapy integrated transducer are implemented as a single element, but the present invention is not limited thereto. For example, the therapy transducer and the imaging transducer may be implemented in an array structure, where applicable array include a linear array probe, a curvilinear probe, a phased array probe, an annular array probe, and a 2-dimensional matrix array probe.

As described above, an imaging and therapy integrated transducer according to an embodiment of the present invention and an ultrasound system including the imaging and therapy integrated transducer may be applied to not only surgery to treat diseases such as skin cancer, liver cancer, cervical cancer, and prostate cancer that require therapy and diagnosis at the same time but also procedures (for example, wrinkle removal procedures) for cosmetic purposes.

The present invention is not limited to the embodiments described above and the accompanying drawings. It will be apparent that those skilled in the art to which the present invention pertains may substitute, modify, and change components according to the present invention without departing from the technical idea of the present invention.

The invention claimed is:

1. An ultrasound system comprising:
   an imaging and therapy integrated transducer including a therapy transducer and an imaging transducer;
   a linear motor module configured to linearly move the imaging and therapy integrated transducer along a therapy target region; and
   a rotation motor module configured to rotate the imaging and therapy integrated transducer to switch the imaging transducer and the therapy transducer,
   wherein the therapy transducer and the imaging transducer are arranged to be switchable to each other by rotation in a housing,
   the rotation motor module comprises a rotary motor shaft on which the imaging and therapy integrated transducer is installed and rotation motors arranged on and connected to both ends of the rotary motor shaft,
   the imaging and therapy integrated transducer is configured to move along the rotary motor shaft in the housing, and
   the imaging and therapy integrated transducer is configured to alternately perform imaging and therapy by rotating by the rotation motors when the imaging and therapy integrated transducer reaches the rotation motors at each end of the rotary motor shaft.

2. The ultrasound system of claim 1, wherein
   the therapy transducer and the imaging transducer have focal depths that are the same as each other or have a difference within a preset range.

3. The ultrasound system of claim 1, wherein
   the therapy transducer has a form in which a conductive material, a piezoelectric element, another conductive material, and a rear surface layer are sequentially stacked, and both sides of the stacked elements may be protected by an epoxy resin.

4. The ultrasound system of claim 1, wherein
the imaging transducer has a form in which a second matching layer, a conductive material, a first matching layer, another conductive material, a piezoelectric element, another conductive material, and a rear surface layer are sequentially stacked, and both sides of the stacked elements are protected by an epoxy resin.

5. The ultrasound system of claim 1, wherein
the imaging and therapy integrated transducer is arranged in a straight line such that the therapy transducer and the imaging transducer face each other in opposite direction based on the rotary motor shaft.

6. The ultrasound system of claim 2, wherein
the rotation motor module is configured to rotate the imaging and therapy integrated transducer by 180 degrees based on the rotary motor shaft such that one of the imaging transducer and the therapy transducer faces the therapy target region.

7. The ultrasound system of claim 3, wherein
the imaging and therapy integrated transducer is configured to image the therapy target region while moving in one direction by the linear motor module in a state in which the imaging transducer faces the therapy target region, and when the imaging and therapy integrated transducer reaches the rotation motor located at one end of the rotary motor shaft, the imaging and therapy integrated transducer is configured to rotate 180 degrees by the rotation motor such that the therapy transducer faces the therapy target region, and the imaging and therapy integrated transducer is configured to perform therapy of the therapy target region while moving in an opposite direction by the linear motor module, and when the imaging and therapy integrated transducer reaches the rotation motor located at the other end of the rotary motor shaft, the imaging and therapy integrated transducer is configured to rotate 180 degrees again by the rotation motor such that the imaging transducer faces the therapy target region, and the imaging and therapy integrated transducer is configured to image the therapy target region while moving in the one direction by the linear motor module.

* * * * *